(12) United States Patent
Edebo

(10) Patent No.: US 6,423,337 B1
(45) Date of Patent: Jul. 23, 2002

(54) POROUS STRUCTURE COMPRISING FUNGI CELL WALLS

(75) Inventor: Lars Edebo, Göteborg (SE)

(73) Assignee: Lizyx AB, Gothenburg (SE)

( * ) Notice: Subject to any disclaimer, the term of this patent is extended or adjusted under 35 U.S.C. 154(b) by 0 days.

(21) Appl. No.: 09/686,456

(22) Filed: Oct. 11, 2000

Related U.S. Application Data

(63) Continuation of application No. PCT/SE99/00604, filed on Apr. 16, 1999.

(30) Foreign Application Priority Data

Apr. 20, 1998 (SE) .............................................. 9801373

(51) Int. Cl.[7] .......................... A61L 15/28; C08B 37/08

(52) U.S. Cl. ....................... 424/445; 424/488; 424/115; 424/122; 435/101; 435/261; 536/20

(58) Field of Search ................................. 435/101, 261; 536/20; 424/445, 488, 115, 122

(56) References Cited

U.S. PATENT DOCUMENTS 6,333,399 B1 * 12/2001 Teslenko et al. .............. 536/20

FOREIGN PATENT DOCUMENTS

| GB | 2188135 A | * | 9/1987 |
| WO | WO 91/05869 | * | 5/1991 |
| WO | WO 96/25437 | * | 8/1996 |

* cited by examiner

*Primary Examiner*—Francisco Prats
(74) *Attorney, Agent, or Firm*—Samuels, Gauthier & Stevens, LLP

(57) ABSTRACT

The present invention relates to a porous structure of prepared fungal cell wall components, whereby the cell wall material is derived from a fungi selected from the division Zygomycota, the fungal material in the form of a suspension is subjected to drying in such a way that the material obtains a porous structure, the structure has a liquid absorbing property which is at least 15 ml/g of 1% NaCl (aq) and it has a liquid transporting ability of water, at a density of 0.01 to 0.03 g/cm$^3$, in a horizontal direction of at least 10 mm during the first minute of absorption and in a vertical direction of at least 5 mm during a first minute of absorption.

20 Claims, 1 Drawing Sheet

POROUS STRUCTURE COMPRISING FUNGI CELL WALLS

This is a continuation of copending application International Application PCT/SE99/00604 filed on Apr. 16, 1999 and which designated the U.S.

TECHNICAL FIELD

The present invention relates to a porous structure comprising fungal cell walls having good absorbing, fluid transporting, as well as macro molecular and micro organism binding properties, methods for producing the same as well as its use i wound and hygienic products, such as products for wound treatment and personal hygiene as well as filtering aid.

BACKGROUND

A material that absorbs large amounts of liquid consists traditionally of cross linked synthetic polymers so called super absorbents (SAP), whereby super absorbents in commercial use within the hygiene product industry consist of cross linked polyacrylates. Today the super absorbents will be used i napkins, sanitary towels and the like. The problem using synthetic absorbents is that they are not biologically degradable. Thus one has lately striven for a good and biologically degradable absorbent.

Super absorbing materials have normally, due to both chemical/physical properties and physical shape a very restricted ability to spread a fluid. In order to increase the spreading ability, carrier fibres are added today, such as cellulose. If there was an absorbent which was self-spreading with regard to the fluid one would be able to exclude or reduce this additive.

Another field of use of the absorbents is in wound treatment products such as compresses and wound bandages. Such products should, besides binding fluid, have properties that prevents bacteria and other micro organisms from growing, propagating and spreading. Bacteria influence the healing coarse of wounds and can be spread to surrounding tissue. It is thus a desire that bandage material can absorb bacteria and bind optional degraded products in an effective manner simultaneously as the liquid of the wound is absorbed.

Fungi comprising chitin and chitosane have turned out to have certain wound healing ability and have thus been used in wound treatment products. A wound treatment bandage is described in U.S. Pat. No. 4,960,413, comprising a bunch of fibres derived from micro fungi having been treated with an alkaline solution only in order to obtain chitin and chitosane. They use hyphae of mould fungi which hyphae are threads which is the mould fungi, and thus utilize only the walls of the cells. This material is directed to unspecific wound healing and does not utilize biological super absorption.

In *J. of Biomed. Material Res.*, vol 28, 1994, pp. 463–469, one has investigated different cultures of fungi as a raw material for chitin and chitosane. Hereby one has treated the material using sodium hydroxide and acetic acid in order to produce as pure a chitin/chitosane material as possible. However, there is no information given that the material obtained could have a good absorbing ability.

Swedish patent having No. 465,678 relates to a fungal cell wall material comprising hexose amine and chitin and chitosane. In the patent it is shown that the material can be used for recovering or eliminating products being negatively charged from water based media. The fungal material can be used e.g., as a selective flocculant and/or ion exchanger for chemical compounds and polymers, e.g., proteins, such as enzymes from aqueous liquids. This material has a compact structure having a restricted liquid absorbing ability.

The object of the present invention is to create a porous structure which absorbs fluid and which, moreover, fulfils above indicated desired features of such a material.

1. Outer foil consisting of a water and gas pervious inert foil. One example is a perforated inert polyethylene foil.
2. Upper layer functioning as a mechanical protection and being pervious to steam. It might also be used for providing an extra stability to the bandage. There is suitably used a foam of some kind, such as an polyurethane foam.
3. Absorption body of fungal cell walls which body is prepared from a suspension of 1 to 3% fungal cell wall material, and being freeze dried.
4. Wound surface layer. A structure which is pervious to wound fluid but prevents regenerating cells to grow into it. One example is a thin, perforated inert polyethylene film.

Figure 1:
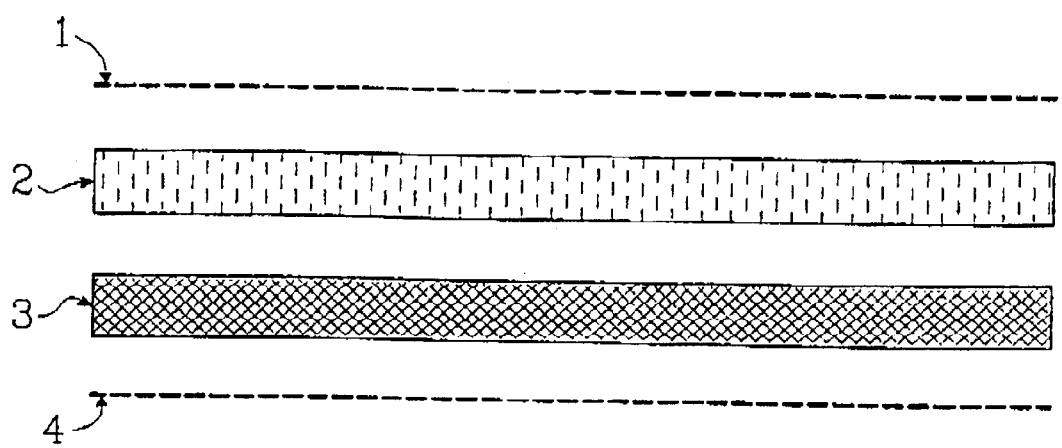
FIG. 1. A schematic sketch of a bandage intended for dry wound surface. The wound surface is present beneath the wound surface layer 4.
Figure 2:
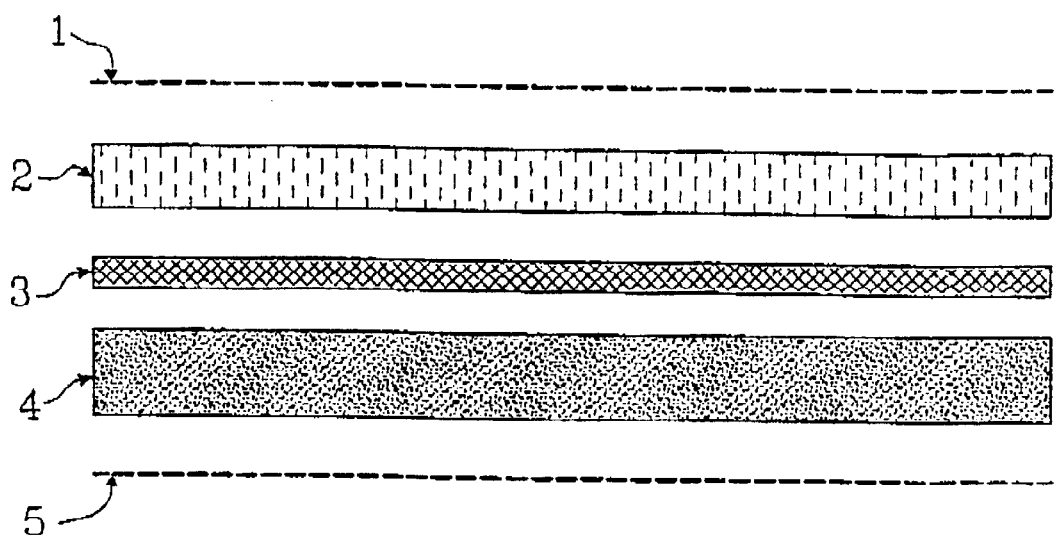

FIG. 2. A schematic sketch of a bandage intended for moist and infected wound surface. The wound surface is present beneath the wound surface layer 4.

1. Outer foil consisting of a water and gas pervious inert foil. One example is a perforated inert polyethylene foil.
2. Upper layer functioning as a mechanical protection and being pervious to steam. It might also be used for providing an extra stability to the bandage. There is suitably used a foam of some kind, such as an polyurethane foam.
3. An extra, super absorbing layer (SAP) intended for excessive amounts of water. Some type of conventional super absorbent, e.g., a micro crystalline cellulose, microbial polysaccharides, alginates or polymeric cross linked acrylates.
4. Absorption body of fungal cell walls which has been prepared from fungal cell wall material being freeze dried mixed with e.g., a fibrous material such as cellulose or alginate.
5. Wound surface layer which is a structure being pervious to wound fluid but prevents regenerating cells to grow into it. One example is a thin, perforated inert polyethylene elm.

SUMMARY OF THE INVENTION

The present invention relates to a porous structure comprising fungal cell walls having good absorbing, fluid transporting, and macro molecular and micro organism binding ability, methods for its preparation, as well as its use in wound and hygiene treatment products.

The porous structure comprises cell wall material of fungi, e.g., belonging to the division Zygomycota comprising hexose amine. The fungi are optionally disintegrated and are then treated in several extraction steps using chemicals, whereupon a suspension is formed. This suspension is dried in such a way that the material obtains a porous structure e.g., using air drying, spray drying or preferably freeze drying. The resulting material obtains a unique capillary system which can absorb and even transport large amounts of liquid as well as absorb proteins, and other macro molecules, and cells e.g, bacteria. The word porous means herein that the material comprises large amounts of air, and not, that it is brittle. The material has low density, at most 0.1 g/cm$^3$, preferably at most 0.05 g/cm$^3$.

The term drying means herein that a certain amount of the water is removed which means that part of or all water is removed from the suspension in order to provide the porous structure.

In the extraction process the cell contents is removed and the cell walls are loosened up, whereby the cell wall forms a fine porous net work optionally divided into a great number of fine threads surrounding the cell wall structure. The fungal cell walls are mainly present as micro tubes as the material is derived from a mycelium, i.e., one might characterize the material as being filamentous.

The material comprises large amounts of air, which, however, can be replaced with a liquid, macromolecules, and cells, e.g., micro organisms. One may also use the porous fungal cell wall structure as an absorbent of liquid and as an absorbent of particles, molecules, and/or cells/organisms. The structure handles free swelling whereby the material maintains its 3-dimensional shape and structure in an efficient way after swelling/absorption in water and shows no sign of decomposition/dissolution, nor after a long time (>1 week). Due to the fine capillary system of the structure it has also the ability of spreading a liquid without the addition of any external fibres.

The material can be dried either as it is or bound to one or more surfaces. The surface can be a foam, or a fibre, e.g., a cellulose of synthetic fibre. If the fibre is an absorbing one a material is obtained having preferably macromolecular/microorganism absorbing character. The material can be affixed to a surface after having been dried. The material can become adsorbed to a surface as well after disintegration of the cell wall threads, such as by means of freeze pressing.

The material can also become doped using polar and negatively charged macromolecules such as a protein, or a charged polysaccharide. By using doping one provides the material with other properties. If one dopes the material using an enzyme, a material is obtained having an enzymatic activity.

The material can further be used i gel form which is obtained by freezing and then thawing a suspension containing the material, which by means of the freezing/thawing operation becomes porous with a retained absorption capability. An advantage using gel form of the material lies in that e.g., a bandage then already contains moist which is advantageous at wound dressings as the moist environment protects from e.g., scare formation. From a production point of view the gel form has advantages as freezing/thawing is a production technical means being more cost effective than freeze drying.

DETAILED DESCRIPTION OF THE INVENTION

The porous structure comprises fungal cell walls comprising polymers of hexose amine, primarily chitin and chitosane (of the division Zygomycota, families Absidia, Mucor, and Rhizopus). The fungi are made subject to an extraction in order to remove lipids, proteins, nucleic acids, and soluble chitosane. Normally, the fungi are disintegrated physically in order to make extraction more simple. According to a suitable process the mycelium is made subject to a) physical disintegration and/or treatment using an organic solvent to remove lipids, and b) treatment using alkali or one or more enzymes to remove proteins and nucleic acid and, if so desired, treatment using an acid to remove soluble chitosane.

A suspension of material is thereby obtained. A method for preparing the suspension of material from which one prepares the porous structure according to the present invention i described in Swedish patent SE-C-465,678. This method is however, only one example and the invention is not restricted to structures prepared according to said method.

There is further a possibility to carry out the extraction directly using alkali and acid.

The suspension is dried in such a way that the material obtains a porous structure, e.g., using air drying or spray drying, but preferably freeze drying. If one allows the material to e.g., become air dried, a less porous structure is normally achieved so that the material loses its "lightness". One may improve the drying properties of the material by adding different additives to the suspension. An alcohol, e.g., isopropanol, can be added which provides for a drying course with solvent exchange. A tenside, e.g., Trition X100 can be added if one wishes to reduce the surface tension of the suspension. The suspension can be acidified to a pH below 7, preferably 3 to 5 in order to promote the introduction of positive charges in the material, and one may even add other compounds in order to change the charging properties and polarity of the final structure.

One may also add macromolecules to the suspension, such as proteins, e.g., enzymes or charged polysaccharides, e.g., heparin. One will then obtain a material having further properties depending upon what has been added. If e.g., an enzyme is added a material is obtained having an enzymatic activity.

The resulting material, in particular the freeze dried one, obtains a unique capillary system, which can absorb and also transport large amounts of liquid. The material has, due to its porous structure a low density which is at most 0,1 g/cm$^3$, preferably at most 0,05 g/cm$^3$. The material thus consequently consists of large amounts of air. The air can be replaced by liquid or biological material. The porous fungal cell wall structure is therefore an excellent absorbent. The structure handles free swelling, whereby the material retains its 3-dimensional form and structure in an efficient way after free swelling/absorption in water and shows no sign of disintegration/dissolution, nor after a long time (>1 week). Due to the fine capillary system of the structure it has also an ability of spreading liquid without the addition of an external fibre. The material absorbs at least 15 ml/g of 1% NaCl (aq) (Example 3).

The material transports rapidly large amounts of liquid. This occurs in a material that consists to a great extent of air. The void volume is at least 80%, preferably at least 90% and more preferably at least 95%. Such low density materials are normally characterized by a high absorption capacity at an active addition of liquid, but a remarkably low transporting ability/spreading. In the fungal cell wall material a widespread system of cell wall tubes connected to each other are present which tubes together creates a continuous system of fine capillary pores which creates the good absorbing ability. In combination with the large void volume which is available to incoming liquid, this leads to a remarkable ability to rapid and voluminous liquid transport. E.g., the liquid transporting ability of water, at an density of 0.01 to 0.03 g/cm$^3$, is at least 10 mm, preferably at least 15 mm, more preferably at least 25 mm in an horizontal direction during the first minute of absorption, and at least 5 mm, preferably at least 10 mm, more preferably at least 20 mm, in a vertical direction during the first minute of absorption (Example 6).

The material has, besides its ability of absorbing and transporting a liquid, also the ability of binding microorganisms, including bacteria and yeast cells, animal cells, macromolecules, e.g., proteins and cell disintegration products, e.g., endotoxins, molecular aggregates, and particles. E.g., the material has a macromolecular binding ability which is at least 0.1 g of bovine serum albumin per gram of fungal cell wall material. Example of the microorganism binding ability of the material is that it binds at least 80% of the bacteria of an suspension comprising 1 mg fungal cell wall material per ml of liquid and $10^8$ $E.$ $coli$ cells per ml of suspension (Example 8).

The material has a pH value of 7, a positive Zeta-potential and/or Zeta-potential of at least 10 mV at pH 6, preferably at least 20 mV at pH 6 when the fungal cell wall material is disintegrated to a particle size less tan 20 $\mu$m. The hexose amine is at least 5% by weight of the fungal cell wall material.

The material can be dried either as it is or bound to one or more surfaces. The surface can be a foam, a film, or a fibre, e.g., cellulose or synthetic fibre. If the fibre has absorbing properties a material is obtained that has liquid absorbing character. If the fibre is a non-absorbing fibre one increases the protein/bacteria/cell binding ability of the material. E.g., if the fibre is made of a resin a material is obtained having preferably protein/bacteria/cell absorbing character. In that way one can modify the structure so that one obtains the right properties with regard to absorption of liquid and absorption of microorganisms.

The material can be attached to a surface as well, after having been dried.

The fungal cell wall material can be used in hygiene treatment products, e.g., napkins, incontinence protection, sanitary towels, and tampons, and in wound treatment products such as e.g., compresses and bandages. Absorbing products such as napkins, incontinence protection and sanitary towels normally consist of several layers. The fungal cell wall material can either become arranged directly beneath a surface material or beneath an inlet/transporting layer, e.g., a "high loft" material. In e.g., napkins, sanitary towels, and incontinence protection the material can be used as an absorption and/or spreading material, as well as an odour protecting agent. In bandages the material can be used for binding bacteria and liquids but if the material has been doped using a protein, e.g., an enzyme, one may add further properties as well.

An example of a bandage where the fungal cell wall material is suitable for use, is an occlusion bandage. The ability of the bandage to absorb liquid can be changed as desired. For example, the capillary force that influences the transport length of the material and the absorption velocity can be regulated by means of modification of the freeze dried fungal cell wall material.

Depending upon which type of bandage that is wanted, the cell wall material can be separated from the wound or not. The constituents of the material, chitosane and chitin, are said to have a stimulating effect upon the wound healing process, why it might be advantageous to let the bring the material in contact with the surface. Bandages can be created for both dry and wet wound surfaces.

Below embodying examples of the present invention are given.

EXAMPLE 1
Preparation of a Porous Structure

Fungal comprising chitosane and chitin were made subject to a physical disintegration and/or were treated using an organic solvent in order to remove lipids. Then the material was treated using alkali and/or an enzyme to remove proteins and nucleic acids. The method is described more in detail in SE-C-465,678.

The suspension was freeze dried using a freeze drier of the so called cheese hood model. It consists of i.a., a vacuo pump and a cooling element, a so called cool trap.

The suspension of the fungal cell wall material was spread to a desired thickness of about 3 to 5 mm, on plates. (The material had the same thickness before ad after the freeze drying step). The plates were covered with a foil, in this case a silicon foil, in order to avoid that the material was attached onto the plate after drying. The plates were placed in a freezer for one or more days, or until the material had become dry.

The material obtained had a very porous structure of the density about 0.01–0.1 g/cm$^3$. The density of the material depended upon which concentration of fungal cell wall material there was in the suspension. E.g., at a concentration of 10 mg fungal cell wall material per ml liquid, a dried material having the density of 0.01 g/cm$^3$ was obtained.

EXAMPLE 2
Preparation of a Porous Structure Bound to a Fibre

Viscose fibres were dipped into the suspension of material according to Example 1. The suspension was stirred. The cell wall material rapidly attached to the fibres. Then the fibres were brought up from the suspension and put onto a net and were dried. If there was a low content of fungal cell wall material on the viscose fibre, i.e., some percent fungal cell wall material based on the viscose fibre the material was able to be dried at room temperature or in a heating cabinet. If a larger amount of fungal cell wall material was present, 10–20%, there was a risk that one obtained problems with hardened parts, i.e., the fungal cell wall material lost its structure. During such conditions the material was preferably dried using freeze or spray drying.

EXAMPLE 3
Preparation of a Macromolecule Doped Porous Structure

The negatively charged macromolecule heparin was added to the suspension of the fungal cell wall material according to Example 1 while being stirred. The macromolecules attached to the cell wall material of the suspension whereupon it was dried in accordance with Example 1.

EXAMPLE 4
Absorption Properties of the Porous Structure

The liquid absorbing property of the porous structure according to Example 1 was tested using 1% NaCl (aq.). The material body was placed onto a fine mesh net and absorbed the liquid by free swelling. The liquid absorption was further tested with regard to retention, which is a measure of how much liquid a material retains under pressure. The material was then placed into a dialyse tube in a centrifuge tube having glass beads on the bottom. The measurement of the material was carried out after centrifugation at 300 g for 10 min. The pore size of the dialyse tube was 0.01 $\mu$m.

Freeze dried fungal cell wall material was investigated and as a reference cellulose and SAP (commercial cross linked polyacrylate, SCA, Mölnlycke, SE) were used. The results are evident from the table below.

TABLE 1

| Material | Absorption-free swelling | Retention-after centrifugation |
|---|---|---|
| Fungal cell wall material (freeze dried) | 40–60 ml/g | 10–25 ml/g |
| Cellulose (fluff mass) | 10–15 ml/g | 1 ml/g |
| SAP (cross-linked polyacrylate) | 50–60 ml/g | 23–33 ml/g |

The value of the fungal cell wall material is, at free swelling, completely comparable to many commercially so called super absorbents. Particularly impressing is the ability of the fungal cell wall material to retain liquid at pressure. This is very uncommon due to the fact that the material has not been cross-linked which is normally a prerequisite for obtaining "super-absorbing" properties.

EXAMPLE 5
Absorption Properties of a Mixture of Fungal Cell Wall Material and Other Absorbing Material in the Form of Cellulose Fibres A suspension of fungal cell wall material was mixed with cellulose fibres (viscose) being suspended in water in such a way that the final content of cell wall material became 12% by weight (dry weight) of the mixture. As a reference a mixture of dry viscose and commercially granulated super-absorbent (cross-linked polyacrylate) was used, which latter was 12% by weight of the mixture. These materials were analysed with regard to absorption in accordance with Example 2. The absorption relates to the total absorption of the fibre body and the calculated absorption relates to the absorption by fungal cell wall material without fibres.

TABLE 2

| Material | Absorption-free swelling, whole body | Calculated absorption by cell wall material only (excl. fibre) | Retention-whole body after centrifugation | Calculated retention without fibre |
|---|---|---|---|---|
| Fungal cell wall material + fibre | 15–20 ml/g | 40–70 ml/g | 7 ml/g | 20–30 ml/g |
| SAP + fibre | 11 ml/g | 50–60 ml/g | 10 ml/g | 25–35 ml/g |

EXAMPLE 6
Distribution of Liquid in a Homogenous Test Body of Freeze Dried Cell Wall Material The dimension of the test body was 54×27×4 mm and 54×27 1.5 mm. The latter test body had been compressed by means of a weight being placed onto the material. Liquid (1% NaCl (aq.)) was added in lots containing 0.3 mls to the short side of the test bodies.

TABLE 3

| Material | Density | Spreading velocity after addition liquid | Total absorption capacity |
|---|---|---|---|
| Uncompressed fungal cell wall material | 0.01 (g/cm$^3$) | 7 mm/min (after 1.0 ml addition) | 3.0 ml correspond to 60 ml/g |

TABLE 3-continued

| Material | Density | Spreading velocity after addition liquid | Total absorption capacity |
|---|---|---|---|
| Compressed fungal cell wall material | 0.02 (g/cm$^3$) | 9 mm/min (after 1.0 ml addition) | 1.8 ml correspond to 35 ml/g |

A test with regard to the ability of the material of active transporting liquid was cited out as well. A test body having the dimensions 50×50×4 mm absorbed a constant flow of liquid (1% NaCl (aq.)). This was done by adding the liquid from above to the centre of the test body using such a flow that it did not overflow until the liquid had reached the short sides of the test body.

TABLE 4

| Material | Density | Spreading velocity after addition of liquid |
|---|---|---|
| Uncompressed fungal cell wall material | 0.008 (g/cm$^3$) | 10 mm/min |
| Compressed fungal cell wall material | 0.017 (g/cm$^3$) | 25 mm/min |

EXAMPLE 7
Raising Height

Using this method a measure of the capacity of the material to transport liquid vertically upwardly by means of the capillary forces, was obtained. Strips of the material having the dimensions 12×1.5 cm were hanged vertically in such a way that the lowest part was situated some millimeters below the liquid surface in a bowl filled with liquid. After lowering the raising height was determined after different time intervals.

Fungal cell wall material: freeze dried material of a 0.5% suspension. Weight 65 mg. Density: 0.014 g/cm$^3$.

TABLE 5

| Time (min) | Raising height (cm) | Total Raising height/min (cm/min) |
|---|---|---|
| 5 | 1.5 | 0.30 |
| 10 | 4.0 | 0.40 |
| 20 | 7.0 | 0.35 |
| 30 | 7.9 | 0.26 |
| 60 | 8.6 | 0.14 |
| 2 hours | 9.4 | 0.08 |
| 4 hours | 11.0 | 0.05 |

As a comparison both cellulose-tissue and Wettex sheet (viscose foam, density 0.13 g/cm$^3$) had a total raising height of 12 cm after 20 min and a raising height velocity of 0.6 cm/min. A compressed fungal cell wall material according to the invention (density 0.022 g/cm$^3$) transported 25 mm of liquid already during the first minute and reached 50 mm after 5 min and 75 mm after 25 min.

Even here the fungal cell wall material exhibited good results with regard to the extremely low density of the material which is normally connected to weak capillary forces. The material exhibits results which up to 7 cm are surprisingly good in comparison with the optimized capillary materials cellulose-tissue and Wettex sheet.

EXAMPLE 8
Binding Capacity of Macromolecules and Microorganisms

In these tests the macromolecule binding ability of the material was tested. Freeze-dried fungal cell wall material absorbed at least 0.1 g of bovine serum albumin per gram of fungal cell wall material. Absorption results of more than 1.0 g of bovine serum albumin per gram fungal cell wall material were obtained as well.

Furthermore, the microorganism binding ability was tested. It was at least 80% in a suspension comprising 1mg of fungal cell wall material and $10^8$ *E. coli* cells per ml. Results showing up to 99% binding were obtained as well.

EXAMPLE 9
Schematic Design of a Bandage

Herein two schematic examples of occlusion bandages are shown. In the bandages, freeze dried fungal cell wall material from suspensions of 1 to 3% fungal cell wall material were used. The density of the freeze dried material can be varied depending upon the content of fungal cell wall material of the suspension. Then the capillaries of the material are affected as well and thereby the absorption and spreading ability. The properties of the material can thus be changed as desired and as given priority to.

Depending on which type of bandage that is wanted the cell wall material can be separated from the wound, or not. The constituents of the material, chitosane and chitin, are said to have a stimulating effect on the wound healing process and thus it can be advantageous that the material is brought into contact with the surface.

A bandage consists of a number of layers which are varied depending on which type of bandage that is wanted.

The wound surface layer has a structure that allows wound liquid to penetrate, but prevents regenerated cells from growing into it. One example is a thin, perforated, inert polyethylene foil.

The upper layer functions as a mechanical shield and is pervious to steam. It may optionally be used for further stabilizing the bandage. A foam of any kind is suitably used, e.g., a polyurethane foam.

Furthermore, one can use an outer film which is a water and gas pervious inert film. One example is a perforated, insert polyethylene film.

For constructing of bandages intended for a dry wound surface one can provide a 5 mm thick, freeze dried fungal cell wall material above the wound surface layer (FIG. 2). Furthermore, one can have an upper layer, in accordance with above, on the top side of the freeze dried fungal cell wall material consisting of a superabsorbent. This layer drains the fungal cell wall layer by means of capillary forces and thus actions a liquid "pump" from the wound surface to the upper side of the bandage. There the liquid is transformed into gas phase and leaves the bandage via an optional outer film. In the same way the superabsorbent layer can easily be removed without removing the fungal cell wall layer, which can disturb the wound healing, in order to eliminate either amounts of wound liquid if the absorbent should become saturated.

An infected and moist wound raises other and higher requirements on absorption capacity of wound liquid as well as capacity with regard to absorption of proteins, cells, cell residues, and other material present in the wound secrete. Hereby it might be suitable to have a layer of freeze dried fungal cell wall material mixed with e.g., a fibrous material such as cellulose or alginate (FIG. 2). Then one creates a more heterogenous material structure having a larger inner active surface and can guarantee the flow of bacteria cells into more peripheral parts of the absorption body. Above the fungal cell wall body one may have a superabsorbent layer of micro crystalline cellulose, microbial polysaccharides, alginates, polymeric cross-linked acrylates. Above this layer one may have an upper layer e.g., a polyurethane foam as well as an outer film.

EXAMPLE 10
Inhibition of Growth of Yeast Fungi

Suspensions of fungal cell wall material were added to yeast cells in such a way that the final concentration became $10^5$–$10^6$ cells/ml. The activity/growth of the microorganisms were quantified via determination of carbon dioxide. Tests using 3.2 mg/ml of fungal cell wall material were carried out for 20 days, others for about 4 days. After the tests the suspensions were cultivated with regard to viability in order to determine if the micro-organisms had become killed by the fungal cell wall material or only become inactivated. The organism used was *Candida albans*.

TABLE 6

|  | Fungal cell wall material (mg/ml) | Growth maximum after (h) |
|---|---|---|
| Positive control |  | 18 |
|  | 4 | 18 |
|  | 8 | 23 |
|  | 16 | 43 |
|  | 32 | no growth |

EXAMPLE 11
Inhibition of Bacterial Growth

The quantification of reduced growth of bacteria in diluted suspensions of the fungal cell wall material according to the invention was made by adding 1 ml of the suspensions to 0.1 ml of bacterial suspension (about 50 bacteria) whereupon the mixtures were shaken for 30 min at room temperature. The suspensions were then moulded into agar-agar plates which were incubated for 5 days at 32° C. whereupon counting of the number of live colonies were done under microscope. References were positive control (nutrient) and weak acetic acid solution (pH 4), respectively.

TABLE 7

| Micro-organism | Pos. control | HAc | Absorbent acc. to invention |
|---|---|---|---|
| *Staph. aureus* | 53 | 38 | 4 |
| *E. coli* | 66 | 2 | 2 |
| *B. subtilis* | 31 | 9 | 6 |

As evident from the table a 92% inhibition of *Staph. aureus* relative to positive control, and 89% relative to acetic acid was determined. With regard to the other two it is difficult to note any difference.

EXAMPLE 12
Odour Elimination

In order to investigate if a preservative effect is at hand using the fungal cell wall material according to the present invention perishable food products (proteinaceous, marine food stuffs) were placed in dilute suspensions of fungal cell wall material of the invention (concentrations: 0.3 to 1.3% by weight=3–13 mg/ml). Pieces of fresh fish and whole, boiled prawns were placed in each 100 ml of suspension according to above at room temperature. As a reference corresponding substrate were placed in equivalent volumes deionized water and in dilute acetic acid, as well. After 24 hrs the test samples were determined subjectively with regard to "unpleasant" odour as an indicium of bacterial activity. The tests were continued with daily determinations.

pH-effect

Tests using fish, and prawns, respectively, placed in dilute acetic acid, solely, were carried in order to determine the effect of pH on the bacterial growth. The substrates were placed in 0.5%, 1.0% and 5%, respectively, acetic acid solutions. 0.5% of HAC was chosen as a reference (zero-sample) as 0.5% HAc has the same pH value (about 3.5) as the fungal cell wall suspensions and the acid effect thereby become 5 days, i.e., it takes further 5 days before a substrate smells bad compared to a reference in water. At a strict arithmetic interpretation the following results are obtained with regard to the effect of fungal cell wall material of the invention=the number of days as the decomposition/unpleasant odour is delayed relative to a sample in 0.5% HAC.

TABLE 8

| Material | Substrate PRAWNS | Substrate FISH |
| --- | --- | --- |
| 0.1% acc. to inv. | no effect | no effect |
| 0.3% acc. to inv. | no effect | 1 day |
| 1.3% acc. to inv. | 15 days | >30 days |

As evident from the table an amount of 1.3% of fungal cell wall material has a strong inhibiting effect on the growth of the micro organisms and proliferation.

EXAMPLE 13

Inhibition of Odour from Urinary Samples

In order to primarily study the possibility of inhibiting the odour of urine at incontinence the series of tests was carried out in which different amounts of freeze dried fungal cell wall material were added to varying amounts of human urine whereafter the samples were placed in plastic boxes with tightening lid at ambient temperature (20° C.). Optional presence of odour was determined subjectively at different time intervals. For comparative purposes a fluff mass and a fluff mass comprising 20% of superabsorbent (SAP) were used as well. The results are shown in Table 9 below.

TABLE 9

| | Test body | Volume added ml/g | Odour (days) |
| --- | --- | --- | --- |
| Results I | acc. to inv. | 20 | 7 (weak) |
| | acc. to inv. | 20 | 8 (weak) |
| | acc. to inv. | 10 | 2 (weak), 3 (strong) |
| Results II | acc. to inv. | 47 | 6 (weak) |
| | acc. to inv. | 49 | 9 (weak) |
| | acc. to inv. | 14 | 8 (weak) |
| | fluff mass | 23 | 1 (weak), 2 (strong) |
| | fluff mass + SAP | 21 | 1 (strong) |

As evident from the table above the fungal cell wall material of the invention has a good inhibiting effect on the development of odour from urine, while napkins, and incontinence protecting means using fluff mass and superabsorbent do not provide any acceptable inhibition of odour.

EXAMPLE 14

Preparation of Porous Material by Means of Freezing/Thawing

As a starting material for the test a fungal cell wall suspension having a dry substance contents of 1.45% by weight was used, which suspension thereby contained 69 ml $H_2O$/g. The suspension was I. frozen in a freezer to $-20°$ C. for 2 days (48 hrs), II. Was thawed in a fridge for 1 day (24 hrs). The originally fluid suspension was, after thawing, present in a well bounded rubberlike structure form, "gel form" having a from the freezing maintained form.

Different basic tests were hereby carried out.

The water evaporation in thawed condition in the refrigerator was determined whereby the following results were obtained.

a) freely exposed material (not covered)

| 24 hrs | 5–7% |
| --- | --- |
| 48 hrs | 20% |
| 72 hrs | 45% |
| 96 hrs | 70% |
| 120 hrs | 85–95% |
| 168 hrs | >95% | b) in covered condition (polyethylene bag)

| 168 hrs | 8–10% |
| --- | --- |

The water evaporation at thawed condition at room temperature (20° C.) was determined whereby the following results were obtained.

a) freely exposed material (non-covered)

| 24 hrs | 10% |
| --- | --- |
| 48 hrs | 30% |
| 72 hrs | 65% |
| 96 hrs | 85–90% |
| 120 hrs | >95% |
| 168 hrs | ≈95%–99% |

Reswelling after some drying was further determined. Hereby 23 g of frozen and thawed gel weighing 2.78 g after 4 days (96 hrs) at room atmosphere. This corresponds to a water content of 7.4 ml/g. The gel was again placed in water (+1% NaCl) for 1 day (24 hrs) whereafter the weight was determined to be 16.0 g which corresponds to 48 ml/g.

I a second test 25 g of gel was taken which were allowed to dry until they were felt "completely dry". It then weighed 0.65 g (after 6 days (144 hrs) in refrigerator). This corresponds to a water content of about 1 ml/g. The gel was then again placed into water (+1% NaCl) for 1 day (24 hrs) whereafter the weight was determined to be 11.0 g, which corresponds to 31 ml/g.

Tests were also carried out using different water concentrations at freezing/thawing of the fungal cell wall suspension. The starting material was a suspension of 1.45% of fungal cell wall material (=69 ml/g) as above. This suspension was diluted serially with water in accordance with the table below (all about 8 ml in total). The samples were then frozen at $-20°$ C. for 2 days (48 hrs) in plastic throughs in such a way that the thickness was 0.5 cm and the surface become 20 $cm^2$. The samples were then allowed to thaw in refrigerator for 1 day (24 hrs). Then the gels obtained were tested with regard to mechanical strength by being lifted in one corner using a pair of tweezers whereby the strength was recorded via a simple YES/NO test.

TABLE 10

| Sample | Dilution | Matr. amount Water content Strength | Dilut. (due to evaporation) |
|---|---|---|---|
| A. | 2× | 0,72% 138 ml/g YES | 1,3 × (90 ml/g) |
| B. | 4× | 0,35% 276 ml/g YES | 2,7 × (186 ml/g) |
| C. | 6× | 0,24% 414 ml/g Partly YES | 3,5 × (242 ml/g) |

The samples were then dried completely in an owen (105° C., 4 hrs).

| Sample | Weight prior to drying (drained gel) | Weight after drying | Water content in gel (before drying) | Dry substance content (before drying) |
|---|---|---|---|---|
| A. | 6,15 g | 0,058 g | 105 ml/g | 0,95% |
| B. | 3,55 g | 0,032 g | 110 ml/g | 0,91% |
| C. | 2,45 g | 0,021 g | 116 ml/g | 0,86% |

A very surprising observation could be made viz. That at freezing of the above suspensions having a low dry substance content the gel forms a core having about 1% by weight of dry substance, independent of ingoing dry substance content. This means that part of the suspension medium will freeze out, that is to say that one obtains a drying of the material suspension. Higher DS contents can of course be obtained using higher ingoing contents of the material suspension, whereby 1 to 12% by weight of DS are suitable, but more preferably 2 to 8% by weight, more preferably 3 to 6% by weight.

Other tests have shown that continuous gels are obtained prior than 2 days at −20° C. at higher concentrations of dry matter. Thus a suspension of 30 ml $H_2O$/g provides a continuous gel after 12 hrs.

What is claimed is:

1. A porous absorbent structure of prepared fungal cell wall material, wherein the cell wall material is derived from a fungus selected from the division Zygomycota, the fungus is treated by an extraction with alkali, followed by an acid extraction, wherein the cell wall material is obtained in dry form by subjecting an acid suspension thereof to drying such that the material obtains a porous structure having a net positive charge at pH 7 after reconstitution with water, whereby the dried material has a liquid absorbing property which is at least 30 ml/g of 1% NaCl (aq) and has a liquid transporting ability of water, at a density of 0.01 to 0.03 g/cm$^3$, in a horizontal direction of at least 10 mm during the first minute of absorption and in a vertical direction of at least 5 mm during a first minute of absorption.

2. The porous absorbent structure according to claim 1, wherein the structure has been obtained by means of freeze or spray drying.

3. The porous absorbent structure according to claim 1, wherein the structure has been obtained by adding an alcohol to the fungal cell wall material suspension before drying thereof, by means of evaporation of the alcohol.

4. The porous absorbent structure according to claim 1, wherein its density is at most 0.1 g/cm$^3$.

5. The porous absorbent structure according to claim 1, wherein it has free swelling of liquid can absorb at least 40 ml/g of 1% NaCl (aq).

6. The porous absorbent structure according to claim 1, wherein it has a liquid transporting ability of a least 8 cm in vertical direction of water in 30 min when the material has the density of 0.014 g/cm$^3$.

7. The porous absorbent structure according to one or more of the preceding claims, wherein the structure has been obtained by freezing/thawing of a suspension of the cell wall material.

8. The porous absorbent structure according to claim 7, wherein it consists of a gel having a dry substance contents of fungal cell wall material which is at least 1% by weight.

9. The porous absorbent structure according to claim 8, wherein the dry substance contents of fungal cell wall material is 1 to 12% by weight.

10. An absorbent comprising a fungal cell wall material according to claim 1 in combination with cellulose fibers or other fibers.

11. The porous structure according to claim 1 wherein the structure is attached to a carrier.

12. A hygiene product in the form of a napkin, incontinence means, sanitary towel or tampon, the hygiene product comprising a liquid absorbing means, said means consisting of a porous structure according to claim 1.

13. Wound treatment means in the form of bandages and compresses comprising liquid absorbing means, said means consisting of a porous structure according to claim 1.

14. Odor eliminating means comprising an odor absorbing means, said means consisting of a porous structure according to claim 1.

15. Bacteria and fungi eliminating means comprising an absorbent means, said means consisting of a porous structure according to claim 1.

16. Microorganism and particle eliminating means comprising an absorbent means, said means consisting of a porous structure according to claim 1.

17. The porous absorbent structure of claim 4, wherein its density is at most 0.05 g/cm$^3$.

18. The porous absorbent structure of claim 9, wherein the dry substance contents of fungal cell wall material is 2 to 8% by weight.

19. The porous absorbent structure of claim 18, wherein the dry substance contents of fungal cell wall material is 3 to 6% by weight.

20. The porous structure of claim 11, wherein the carrier is negatively charged and/or has polarity.

* * * * *